(12) United States Patent
Zucherman et al.

(10) Patent No.: US 6,652,527 B2
(45) Date of Patent: Nov. 25, 2003

(54) SUPPLEMENTAL SPINE FIXATION DEVICE AND METHOD

(75) Inventors: James F. Zucherman, San Francisco, CA (US); Ken Y. Hsu, San Francisco, CA (US); Charles J. Winslow, Walnut Creek, CA (US); Steve Mitchell, Pleasant Hill, CA (US); Scott Yerby, Montara, CA (US); Henry A. Klyce, Piedmont, CA (US)

(73) Assignee: St. Francis Medical Technologies, Inc., Concord, CA (US)

( * ) Notice: Subject to any disclaimer, the term of this patent is extended or adjusted under 35 U.S.C. 154(b) by 2 days.

(21) Appl. No.: 09/982,418

(22) Filed: Oct. 18, 2001

(65) Prior Publication Data

US 2002/0116000 A1 Aug. 22, 2002

Related U.S. Application Data

(63) Continuation-in-part of application No. 09/842,819, filed on Apr. 26, 2001, and a continuation-in-part of application No. 09/579,039, filed on May 26, 2000, now Pat. No. 6,451,019, which is a continuation-in-part of application No. 09/473,173, filed on Dec. 28, 1999, now Pat. No. 6,235,030, which is a continuation of application No. 09/179,570, filed on Oct. 27, 1998, now Pat. No. 6,048,342, which is a continuation-in-part of application No. 09/175,645, filed on Oct. 20, 1998, now Pat. No. 6,068,630

(60) Provisional application No. 60/306,262, filed on Jul. 18, 2001.

(51) Int. Cl.[7] .............................................. A61B 17/70
(52) U.S. Cl. ......................................................... 606/61
(58) Field of Search ............................. 606/61, 60, 72, 606/70, 71, 74; 623/17.11, 17.16

(56) References Cited

U.S. PATENT DOCUMENTS 2,677,369 A 5/1954 Knowles
3,426,364 A 2/1969 Lumb
3,648,691 A 3/1972 Lumb et al.

(List continued on next page.)

FOREIGN PATENT DOCUMENTS

| CA | 2015507 | 1/1991 |
|---|---|---|
| DE | 2821678 A1 | 4/1980 |
| DE | 3113142 A1 | 1/1982 |

(List continued on next page.)

OTHER PUBLICATIONS

Minns, R.J., et al., *Preliminary Design and Experimental Studies of a Novel Soft Implant for Correcting Sagittal Plane Instability in the Lumbar Spine*, SPINE vol. 22, No. 16, pp. 1819–1825, © 1997, Lippincott–Raven Publishers.

Haruo Tsuji, et al., *Ceramic Interspinous Block (CISB) Assisted Anterior Interbody Fusion*, Journal of Spinal Disorders, vol. 3, No. 1, pp. 77–86, ©1990 Raven Press, Ltd., New York.

Richard W. Porter, MD, FRCS, FRCSE, *Spinal Stenosis and Neurogenic Claudication*, SPINE vol. 21, No. 17, pp. 2046–2052, ©1996, Lippincott–Raven Publishers.

*Primary Examiner*—Pedro Philogene
(74) *Attorney, Agent, or Firm*—Fliesler Dubb Meyer & Lovejoy, LLP

(57) ABSTRACT

The implant device is a minimally invasive device for assisting in the fusing together of vertebral bodies of the spine. The implant device immobilizes the vertebral bodies by immobilizing the respective spinous process extending from the vertebral body. The implant device has at least one spacer and hook to immobilize adjacent spinous processes. The spacer and hook are fastened to connection rods. Each connection rod can individually traverse through a range of motion, allowing each hook to engage the respective spinous process.

105 Claims, 12 Drawing Sheets

U.S. PATENT DOCUMENTS

| | | | |
|---|---|---|---|
| 3,867,728 A | 2/1975 | Stubstad et al. | |
| 3,875,595 A | 4/1975 | Froning | |
| 4,309,777 A | 1/1982 | Patil | |
| 4,349,921 A | 9/1982 | Kuntz | |
| 4,369,769 A | 1/1983 | Edwards | |
| 4,401,112 A | 8/1983 | Rezaian | |
| 4,479,491 A | 10/1984 | Martin | |
| 4,501,269 A | 2/1985 | Bagby | |
| 4,553,273 A | 11/1985 | Wu | |
| 4,554,914 A | 11/1985 | Kapp et al. | |
| 4,599,084 A | 7/1986 | Nashef | |
| 4,599,086 A | 7/1986 | Doty | |
| 4,604,995 A | 8/1986 | Stephens et al. | |
| 4,611,582 A | 9/1986 | Duff | |
| 4,636,217 A | 1/1987 | Ogilvie et al. | |
| 4,643,178 A | 2/1987 | Nastari et al. | |
| 4,657,550 A | 4/1987 | Daher | |
| 4,685,447 A | 8/1987 | Iversen et al. | |
| 4,696,290 A | 9/1987 | Steffee | |
| 4,714,469 A | 12/1987 | Kenna | |
| 4,743,256 A | 5/1988 | Brantigan | |
| 4,772,287 A | 9/1988 | Ray et al. | |
| 4,790,303 A | 12/1988 | Steffee | |
| 4,834,757 A | 5/1989 | Brantigan | |
| 4,878,915 A | 11/1989 | Brantigan | |
| 4,904,260 A | 2/1990 | Ray et al. | |
| 4,904,261 A | 2/1990 | Dove et al. | |
| 4,913,134 A | 4/1990 | Luque | |
| 4,932,975 A | 6/1990 | Main et al. | |
| 4,936,848 A | 6/1990 | Bagby | |
| 4,946,378 A | 8/1990 | Hirayama et al. | |
| 4,961,740 A | 10/1990 | Ray et al. | |
| 4,969,888 A | 11/1990 | Scholten et al. | |
| 5,010,879 A * | 4/1991 | Moriya et al. | 606/61 |
| 5,011,484 A | 4/1991 | Breard | |
| 5,015,247 A | 5/1991 | Michelson | |
| 5,026,373 A | 6/1991 | Ray et al. | |
| 5,035,716 A | 7/1991 | Downey | |
| 5,047,055 A | 9/1991 | Bao et al. | |
| 5,055,104 A | 10/1991 | Ray | |
| 5,059,193 A | 10/1991 | Kuslich | |
| 5,059,194 A | 10/1991 | Michelson | |
| 5,084,049 A | 1/1992 | Asher et al. | |
| 5,092,866 A | 3/1992 | Breard et al. | |
| 5,123,926 A | 6/1992 | Pisharodi | |
| 5,167,662 A | 12/1992 | Hayes et al. | |
| 5,180,381 A | 1/1993 | Aust et al. | |
| 5,192,327 A | 3/1993 | Brantigan | |
| 5,258,031 A | 11/1993 | Salib et al. | |
| 5,263,953 A | 11/1993 | Bagby | |
| 5,290,312 A | 3/1994 | Kojimoto et al. | |
| 5,304,178 A | 4/1994 | Stahurski | |
| 5,306,309 A | 4/1994 | Wagner et al. | |
| 5,352,225 A * | 10/1994 | Yuan et al. | 606/61 |
| 5,387,213 A | 2/1995 | Breard et al. | |
| 5,390,683 A | 2/1995 | Pisharodi | |
| 5,395,372 A | 3/1995 | Holt et al. | |
| 5,415,661 A | 5/1995 | Holmes | |
| 5,443,514 A | 8/1995 | Steffee | |
| 5,458,638 A | 10/1995 | Kuslich et al. | |
| 5,458,641 A | 10/1995 | Ramirez Jimenez | |
| 5,458,643 A | 10/1995 | Oka et al. | |
| 5,470,333 A | 11/1995 | Ray | |
| 5,476,462 A * | 12/1995 | Allard et al. | 606/60 |
| 5,476,464 A * | 12/1995 | Metz-Stavenhagen et al. | 606/61 |
| 5,496,318 A | 3/1996 | Howland et al. | |
| 5,505,732 A | 4/1996 | Michelson | |
| 5,514,180 A | 5/1996 | Heggeness et al. | |
| 5,534,028 A | 7/1996 | Bao et al. | |
| 5,534,029 A | 7/1996 | Shima | |
| 5,540,689 A | 7/1996 | Sanders et al. | |
| 5,549,679 A | 8/1996 | Kuslich | |
| 5,562,736 A | 10/1996 | Ray et al. | |
| 5,593,409 A | 1/1997 | Michelson | |
| 5,609,634 A | 3/1997 | Voydeville | |
| 5,645,597 A | 7/1997 | Krapiva | |
| 5,645,599 A | 7/1997 | Samani | |
| 5,653,761 A | 8/1997 | Pisharodi | |
| 5,674,295 A | 10/1997 | Ray et al. | |
| 5,674,296 A | 10/1997 | Bryan et al. | |
| 5,676,702 A | 10/1997 | Ratron | |
| 5,702,455 A | 12/1997 | Saggar | |
| 5,725,582 A | 3/1998 | Bevan et al. | |
| 5,766,252 A | 6/1998 | Henry et al. | |
| 5,824,098 A | 10/1998 | Stein | |
| 5,865,846 A | 2/1999 | Bryan et al. | |
| 5,885,299 A | 3/1999 | Winslow et al. | |
| 5,888,224 A | 3/1999 | Beckers et al. | |
| 5,888,226 A | 3/1999 | Rogozinski | |
| 5,976,186 A | 11/1999 | Bao et al. | |
| 6,001,130 A | 12/1999 | Bryan et al. | |
| 6,022,376 A | 2/2000 | Assell et al. | |
| 6,113,639 A | 9/2000 | Ray et al. | |
| 6,156,067 A | 12/2000 | Bryan et al. | |
| 6,234,705 B1 | 5/2001 | Troxel | |
| 6,451,019 B1 * | 9/2002 | Zuckerman et al. | 606/61 |

FOREIGN PATENT DOCUMENTS

| | | |
|---|---|---|
| EP | 140790 A2 | 10/1984 |
| EP | 146347 A1 | 12/1984 |
| EP | 322334 A1 | 12/1988 |
| EP | 0677277 A2 | 10/1995 |
| EP | 0767636 B1 | 4/1997 |
| EP | 1138268 | 4/2001 |
| FR | WO 90/00037 | 1/1990 |
| FR | 2681525 A1 | 3/1993 |
| FR | 2707864 A1 | 1/1995 |
| FR | 2717675 | 9/1995 |
| FR | 2722980 A1 | 2/1996 |
| FR | 2780269 A1 | 12/1999 |
| FR | 2782911 A1 | 3/2000 |
| FR | 2806614 | 9/2001 |
| FR | 2806616 | 9/2001 |
| SU | 1484348 A1 | 6/1989 |
| WO | WO 91/16018 | 10/1991 |
| WO | WO 94/21185 | 9/1994 |
| WO | WO 94/26192 | 11/1994 |
| WO | WO 98/48717 | 11/1998 |
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 A1 | 4/2001 |

* cited by examiner

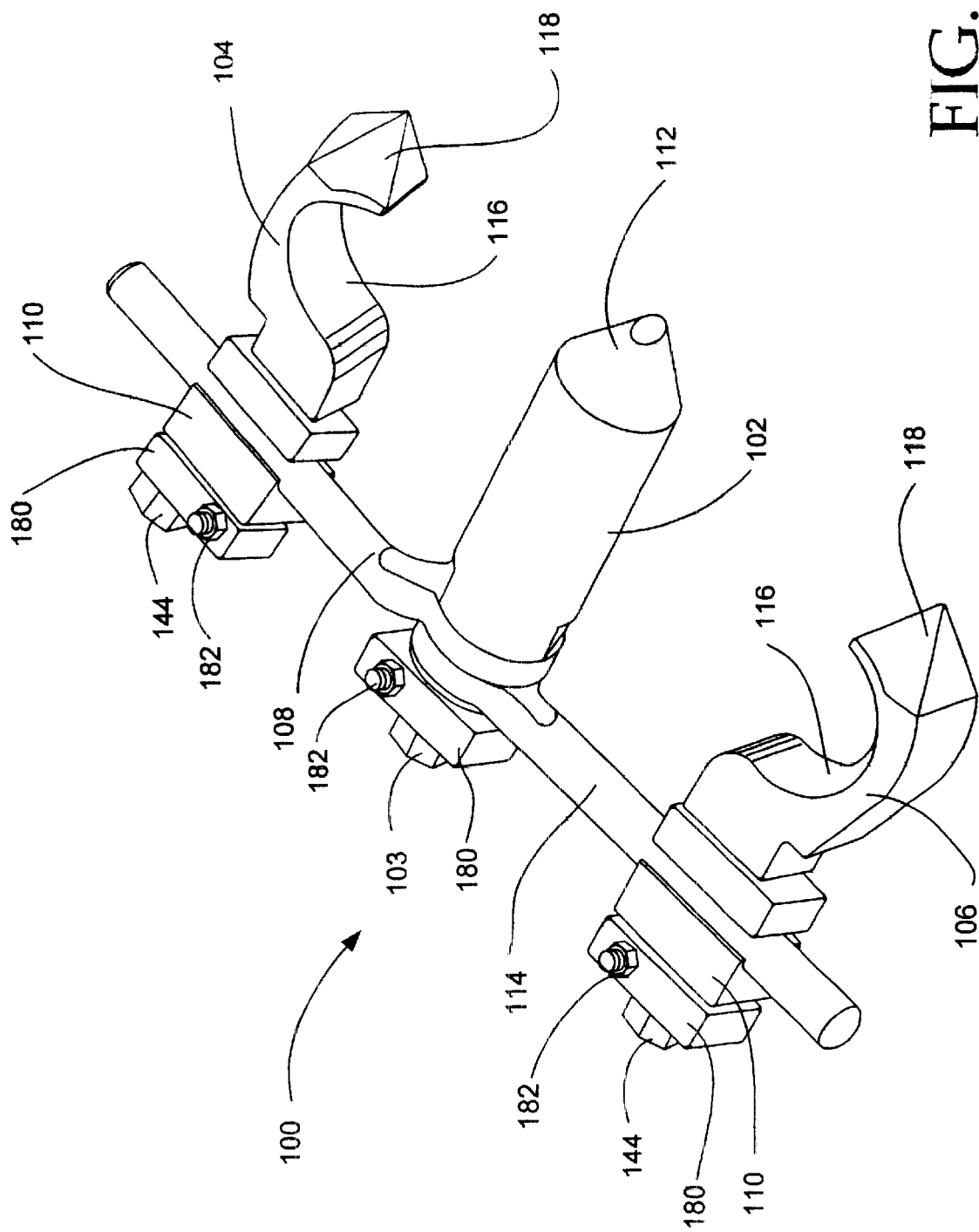

SUPPLEMENTAL SPINE FIXATION DEVICE AND METHOD

CROSS REFERENCE TO RELATED APPLICATIONS

This application claims priority to United States Provisional Patent Application entitled SUPPLEMENTAL SPINE FIXATION DEVICE AND METHOD, filed Jul. 18, 2001, Ser. No. 60/306,262 and is a continuation-in-part application of U.S. patent application Ser. No. 09/842,819, filed Apr. 26, 2001 and is a continuation-in-part application of U.S. patent application Ser. No. 09/579,039, filed on May 26, 2000 and entitled SUPPLEMENTAL SPINE FIXATION DEVICE AND METHOD, now U.S. Pat. No. 6,451,019 which is a continuation-in-part of U.S. patent application Ser. No. 09/473,173 filed on Dec. 28, 1999 and entitled SPINE DISTRACTION IMPLANT, now U.S. Pat. No. 6,235,030 issued May 22, 2001, which is a continuation of U.S. patent application Ser. No. 09/179,570 filed on Oct. 27, 1998 and entitled SPINE DISTRACTION IMPLANT, now U.S. Pat. No. 6,048,342 issued Apr. 11, 2000, which is a continuation-in-part of U.S. patent application Ser. No. 09/175,645 filed on Oct. 20, 1998 and entitled SPINE DISTRACTION IMPLANT, now U.S. Pat. No. 6,068,630 issued May 30, 2000. All of the above applications and patents are incorporated herein by reference.

FIELD OF THE INVENTION

The present invention is directed to supplemental spine fixation devices and methods which are used as an adjunct to a primary spine fusion method and/or device, such as by way of example only, an inter-body fusion device. The present invention is also directed to a method and apparatus for engaging adjacent spinous processes without the use of a primary spinal fusion method or device.

BACKGROUND

A common procedure for handling pain associated with degenerative spinal disk disease is the use of devices for fusing together two or more adjacent vertebral bodies. The procedure is known by a number of terms, one of which is inter-body fusion. Inter-body fusion can be accomplished through the use of a number of devices and methods known in the art. These include screw arrangements, solid bone implant methodologies, and fusion devices which include a cage or other mechanism which is packed with bone and/or bone growth inducing substances. All of the above are implanted between adjacent vertebral bodies in order to fuse the vertebral bodies together, alleviating associated pain.

Associated with such primary fusion devices and methods are supplemental devices which assist in the fusion process. These supplemental devices assist during the several month period when bone from the adjacent vertebral bodies is growing together through the primary fusion device in order to fuse the adjacent vertebral bodies. During this period it is advantageous to have the vertebral bodies held immobile with respect to each other so sufficient bone growth can be established.

Such supplemental devices can include hook and rod arrangements, screw arrangements and a number of other devices which include straps, wires, and bands, all of which are used to immobilize one portion of the spine relative to another. All of these devices generally require extensive surgical procedures in addition to the extensive procedure surrounding the primary fusion implant.

It would be advantageous if the device and procedure for supplemental spine fixation were as simple and easy to perform as possible, and were designed to leave intact as much bone, ligament, and other tissue which comprise and surround the spine, as possible.

SUMMARY OF THE INVENTION

The present invention is directed to providing a supplemental spine fixation device and method for alleviating discomfort associated with the spine and as an adjunct, if desired, to a primary spine fusion technique.

The present invention provides for a method and apparatus for assisting in the fusing together of vertebral bodies of the spine. One of the features and purposes of the invention is to immobilize the vertebral bodies while spine fusion is accomplished. Fusion can require upwards of six months for bone cells from the upper and lower vertebral bodies to grow towards each other, generally through a primary fusion device.

In order to assist in the fusing process, the supplemental spinal fixation device and method of the invention immobilizes the vertebral bodies by immobilizing the respective spinous processes extending therefrom. The present device and method of the invention is minimally invasive such that it does not add to the trauma of the primary fusion procedure, especially if the fusion procedure is from a posterior approach. With an anterior fusion approach, additional posterior incisions are required. However, these are minimal when compared to other devices and methods.

It is also to be understood that the apparatus and method of the present invention can be used without spinal fusion in order to immobilize the spinous processes.

Accordingly, an object of the present invention is to increase the rigidity and stability with respect to the adjacent spinous process and vertebral bodies in order to promote inter-body fusion between the vertebral bodies. A further object is to provide for such rigidity and stability without interbody fusion. For example the embodiment of the present invention can be used with an inventive spinous process distraction mechanism.

It is yet a further object of the present invention to provide for an implant and method which does not require modification of the bone, ligaments, or adjoining tissues. In other words, it is an object of the present invention to provide for an implant and method which does not require that the bone be reshaped, notched, or in anyway modified. It is also an object that there is as little modification as possible to soft tissue and ligaments surrounding the bone.

It is a further object of the present invention to provide for an implant and method which can be inserted from one side of adjacent spinous processes in order to immobilize the spinous processes and resultingly immobilize the adjacent vertebral bodies. By addressing the spinous processes from one side, the objects and advantages of a minimally invasive procedure with reduced trauma, can be accomplished.

It is yet a further object of the present invention to provide for a device which has securing and/or hook elements which can easily and conveniently be secured about the spinous processes, which hook devices are preferably designed in order to accommodate the shape of the spinous processes and preferably swivel or pivot in order to accommodate the position and shape of one spinous processes relative to another.

It is yet another object of the present of the invention to provide for a device which has several degrees of freedom in order to allow a portion of the device to be positioned between spinous processes in order to distract part the spinous processes and other portions of the device to engage the spinous processes in order to rigidly immobilize the spinous processes. These degrees of freedom allow the device to conform to the bones, ligaments, and tissues of each individual patient. Thus, the present device allows for adjustments along two and three axis in order to successfully immobilize spinous processes.

It is yet another object of the invention to provide a device and method for securing together adjacent spinous processes which device is rigid and can keep the spinous processes aligned.

Other aspects, objects and advantages of the invention are evident from the specification, the claims and the figures.

BRIEF DESCRIPTION OF THE DRAWINGS

FIG. 8 is a perspective view of an embodiment of the present invention, illustrating the fastening bolts in an alternative arrangement

FIG. 9a is a front view of an embodiment of the clamp of the present invention; FIG. 9b is a cross-sectional view of the clamp in FIG. 9a through line A—A; FIG. 10a is a top view of an embodiment of the connection rod of the present invention; FIG. 10b is a partial cross-sectional view of the connection rod in FIG. 9a through line A—A.

DETAILED DESCRIPTION OF THE INVENTION

Figure 1:
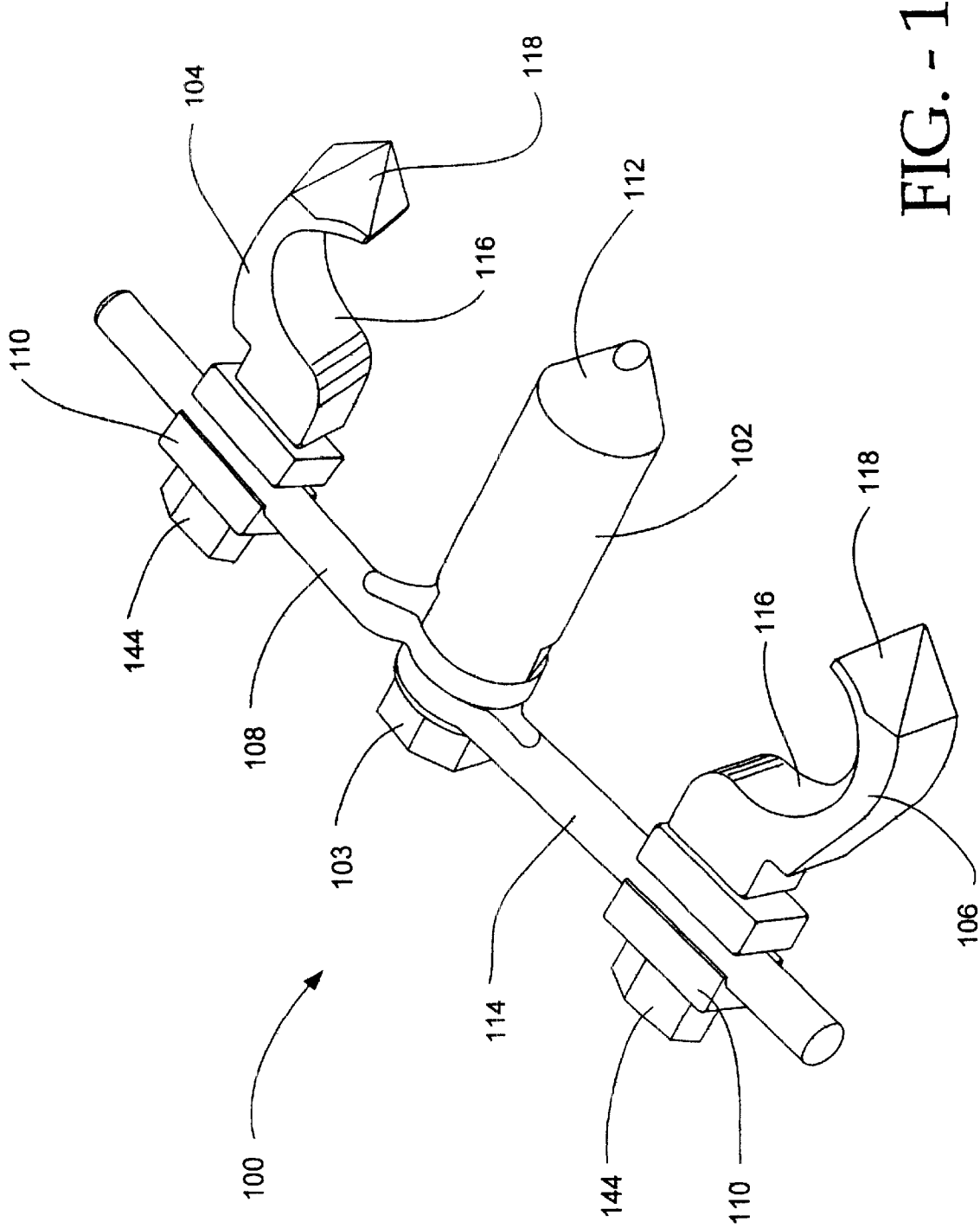
FIG. 1 is a perspective view of an embodiment of the present invention.
Figure 2:
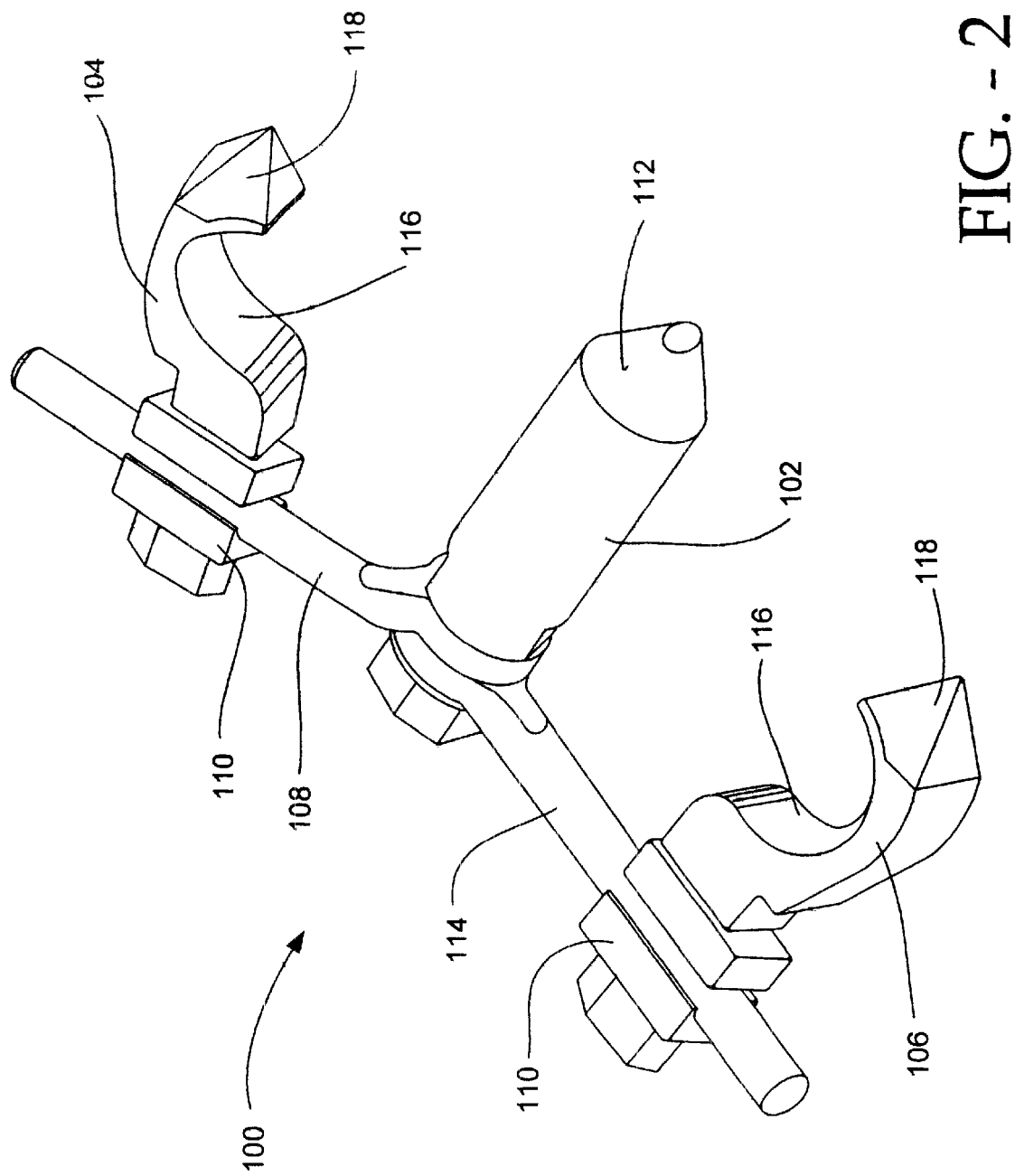
FIG. 2 is a perspective view of an embodiment of the present invention of FIG. 1 illustrating the mobility of the connection rods.
Figure 3:
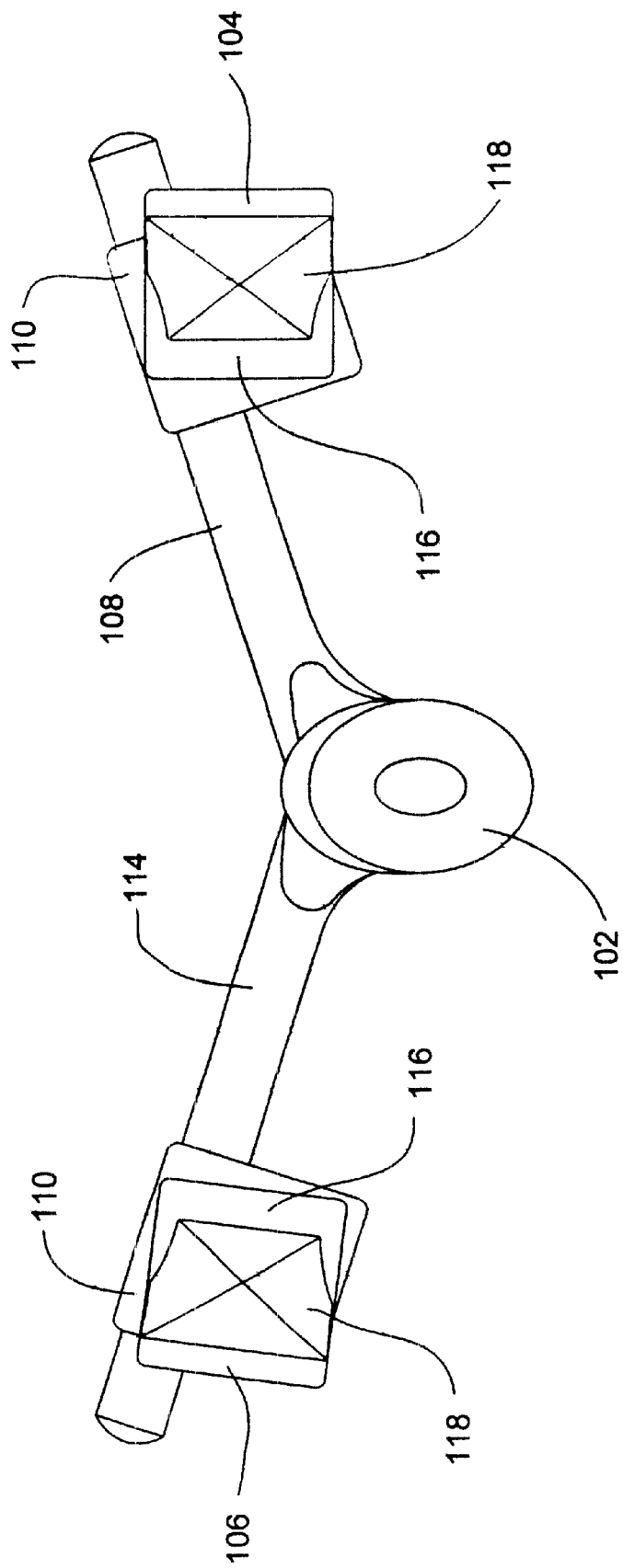
FIG. 3 is a front view of an embodiment of the present invention of FIG. 1.
Figure 4:
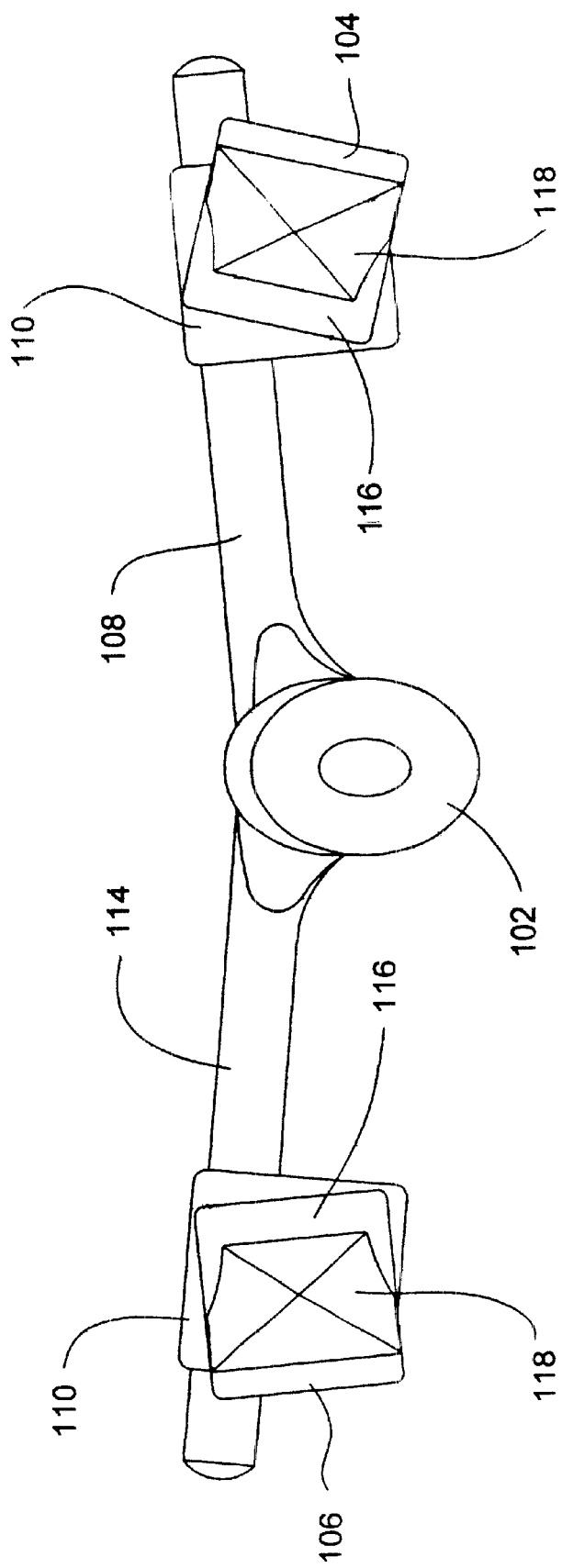
FIG. 4 is a front view of an embodiment of the present invention of FIG. 1 illustrating that the engagement members can individually rotate.

Referring to FIGS. 1–4, the implant device 100 has a spacer 102, a first rotatable engagement element or hook 104, a second rotatable engagement element or hook 106, a first connection rod 108, a second connection rod 114, and clamps 110. By way of example only, these elements may be manufactured from stainless steel, titanium or any other biologically acceptable material.

The spacer 102 in FIG. 1 is substantially cylindrical in shape with an elliptical cross-section and a small diameter and a large diameter. The small diameter provides the height or distance between spinous processes. The small diameter of the spacer 102 is, by way of example only, 6 mm, 8 mm, 10 mm, 12 mm, and 14 mm. Additionally, the spacer 102 may consist of other shapes in cross-section such as, but not limited to, egg-shaped, oval or circular. In a preferred embodiment until locked in place by bolt 103, the spacer 102 can rotate so that it may accommodate the shape of the spinous process it contacts.

Figure 6:
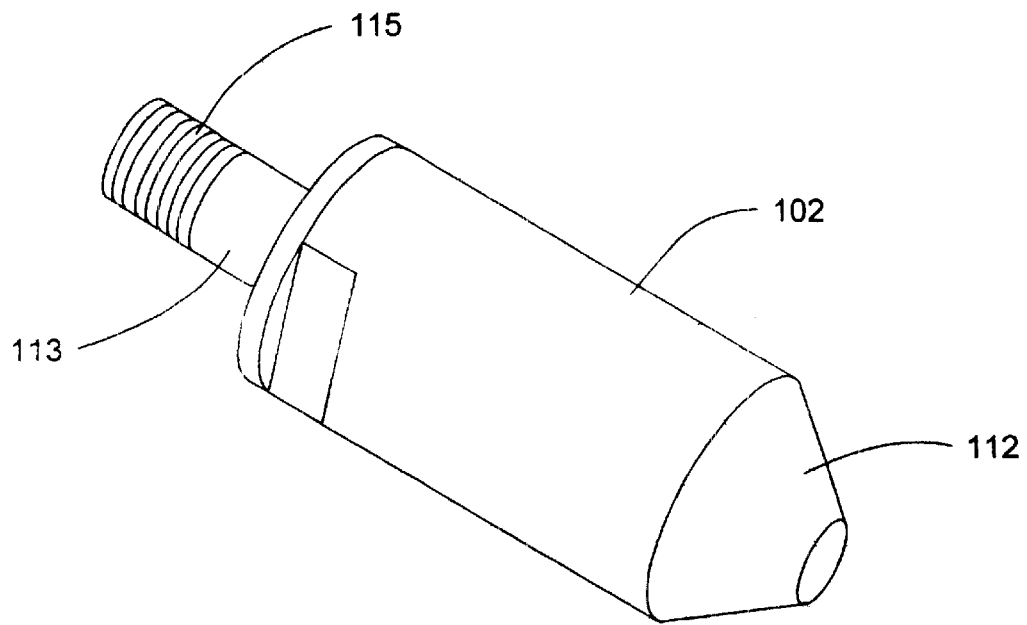
FIG. 6 is a perspective view of an embodiment of the spacer of the invention of FIG. 1.

The spacer 102 also has a tapered front end, lead-in guide, or tissue expander 112, a stem 113 and a threaded section 115 (See FIG. 6). As previously mentioned, the spacer 102 is placed between adjacent spinous process. Thus, the spacer 102 must be urged through the interspinous ligament. A physician will make an initial opening in the interspinous ligament to prepare the area for the spacer 102. The tapered front end 112 minimizes the size of the initial opening a physician must make in the interspinous ligament. The tapered front end 112 can fit into the small initial opening and then distract the interspinous ligament to a height substantially equal to the small diameter of the spacer 102 as the spacer 102 is completely urged through the interspinous ligament. Thus, the tapered front end 112 minimizes trauma to the ligament tissue which promotes a faster recovery.

The spacer 102 is attached with the first connection rod 108 and the second connection rod 114 by the bolt 103. Until tightened, the bolt 103 allows the first and second connection rods 108, 114 to rotate relative to the spacer (see FIG. 2). This allows the hooks 104, 106 to engage a spinous process that are at different angles and distances relative to the spacer 102.

Figure 7:
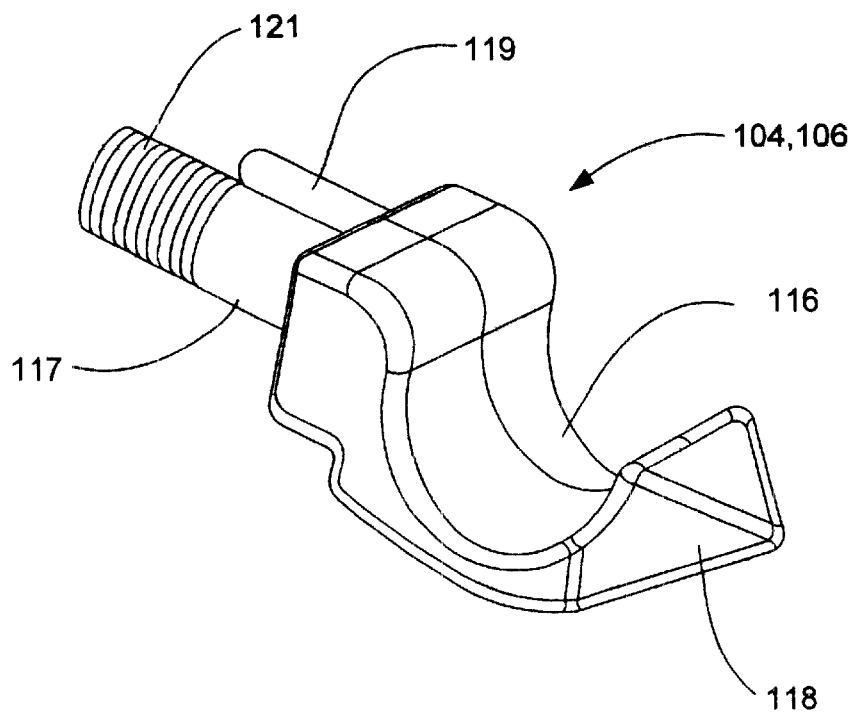
FIG. 7 is a perspective view of an embodiment of the rotatable engagement elements of the invention of FIG. 1.

The first and second hook 104, 106 (FIG. 1) have an engagement element 116, a tapered front end 118 and a stem 117 with a movement limiter 119 (FIG. 7). The tapered front end 118 is adapted for urging between adjacent spinous processes. Similar to the spacer 102, the front end 118 includes a tip or pyramid. This tip or pyramid allows a physician to make a minimal initial opening in the interspinous ligament where the hook 104, 106 will be inserted. The front end 118 is urged into the initial opening and will distract the opening as the hook 104, 106 engages the spinous process. By creating a small initial opening, the tapered front end 118 allows the first and second hook 104, 106 to be inserted between adjacent spinous processes while minimizing the damage to the interspinous ligament tissue.

Figure 11:
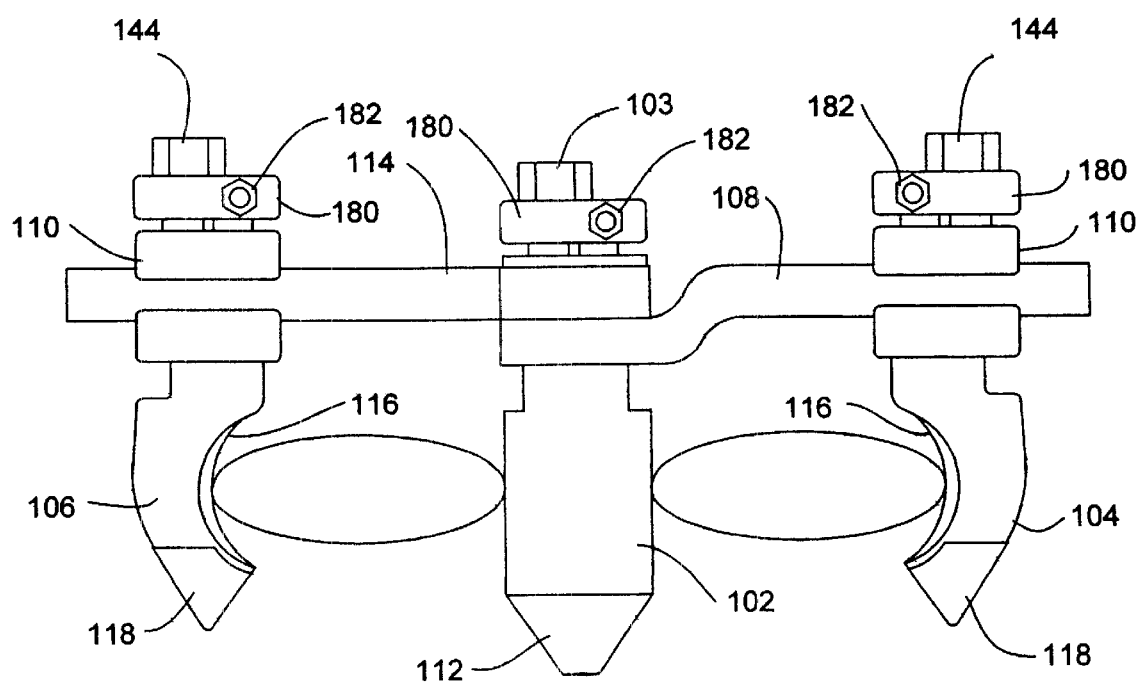
FIG. 11 depicts the embodiment of the invention of FIG. 1 implanted between adjacent spinous processes.

Preferably, the engagement element 116 is U-shaped. One of ordinary skill in the art will appreciate that the engagement element 116 may comprise other shapes such as, but not limited to, rectangular and triangular. The engagement element 116 is intended to be positioned substantially around the spinous process (FIG. 11) such that the engagement element 116 will restrain the spinous processes from movement caused by bending forward. The shape of the first and second hook 104, 106 are such that the spinous processes do not need to be altered or cut away in any manner in order to accommodate the present invention. This is an improvement over the prior art because many prior devices require altering the spinous processes, such as cutting notches or grooves in the spinous processes. Further, the implant device 100 requires little if any altering to the ligaments and soft tissues surrounding the spinous processes. Generally, at most, ligaments would be pierced and/or urged apart. Altering the spinous processes in any manner can weaken the structure and can lead to complications in the future.

Figure 10A:
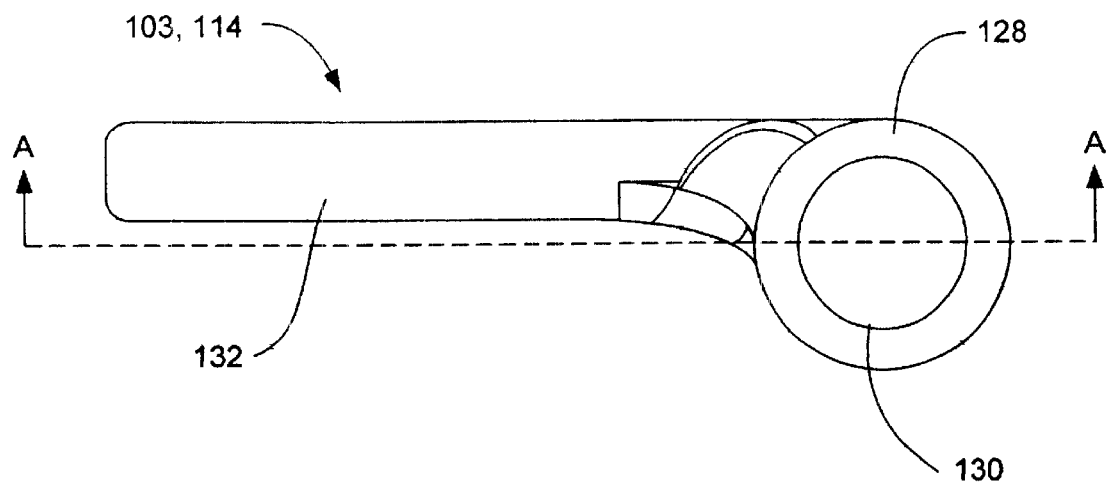
FIGS. 10a and 10b.
Figure 10B:
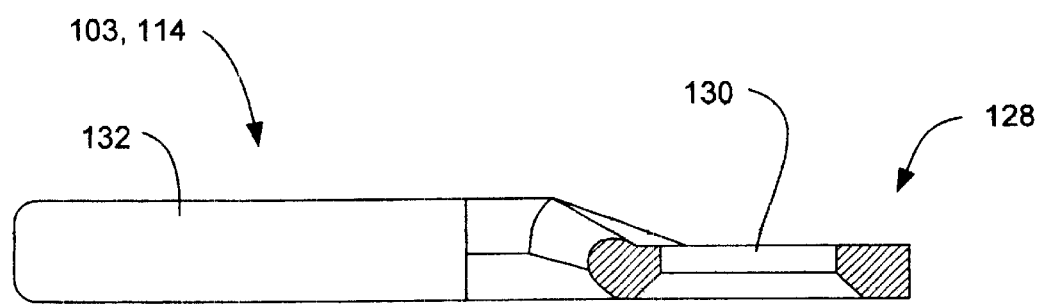

The first and second connection rod 108, 114 have a first end 128 and a second end 132. The first end 128 has a bore 130 extending through (See FIGS. 10a and 10b). The spacer 102 is connected to both the first and second connection rods 108, 114. To attach the spacer 102 with the first and second connection rod 108, 114, the stem 113 (see FIG. 6) of the spacer 102 is inserted through the bore 130 of each connection rod 108, 114. The spacer 102 is then secured to the first and second connection rod 108, 114 by engaging the bolt 103 with the threaded portion 115 of the stem 113. With the bolt 103 fastened to the stem 115, the first and second connection rod 108, 114 can pivot about the longitudinal axis of the spacer 102. The spacer 102 can also rotate as indicated above. Fully tightening bolt 103 fixes the position of the spacer 102 and the connection rods 108, 114.

Figure 9A:
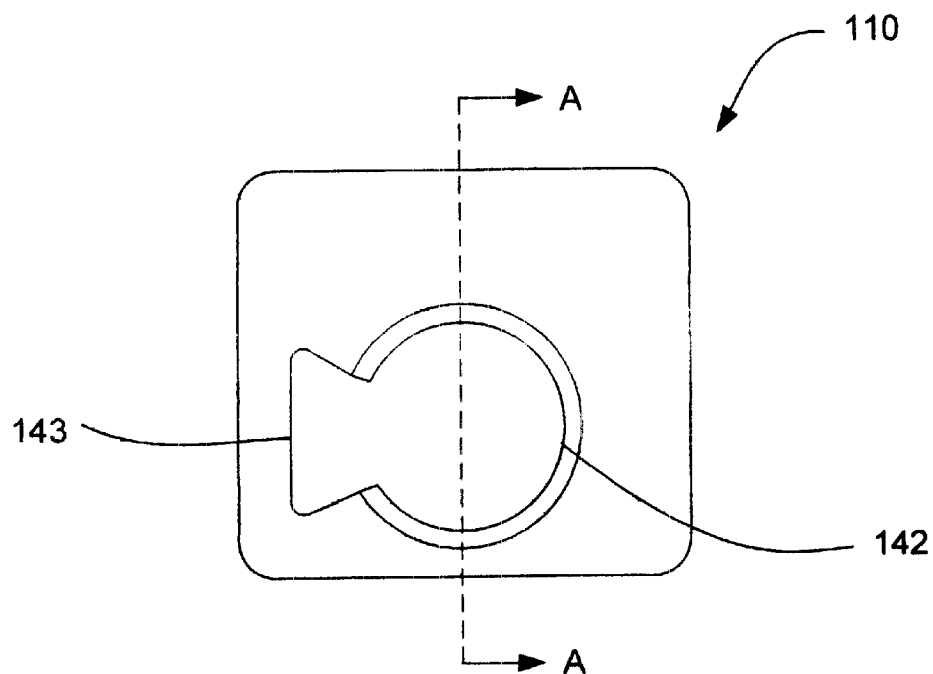
FIGS. 9a and 9b.
Figure 9B:
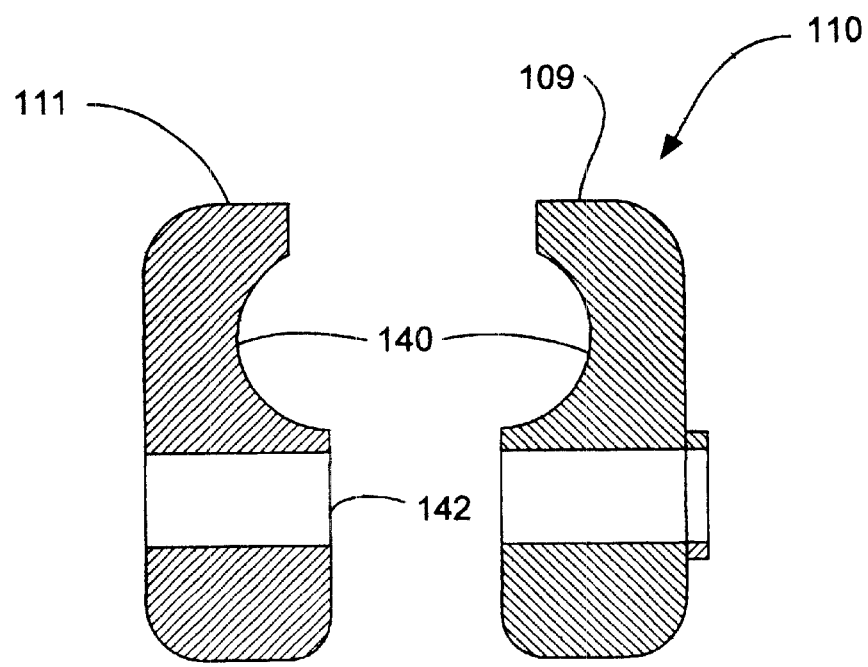

The first hook 104 is also connected with the second end 132 of the first connection rod 108. The hook 104 is secured to the connection rod 108 by clamp 110. As illustrated in FIGS. 9a and 9b, the clamp 110 includes clamping elements 109 and 111, each of which has a channel 140 and a bore 142 extending through. The bore 142 has a limiting cavity 143. The diameter of the two channels 140 is substantially similar to the diameter of the first connection rod 108. The diameter of the bore 142 is substantially similar to the diameter of the stem 117 of the first hook 104.

The clamp 110 is slidably attached with the first connection rod 108. The stem 117 of the first hook 104 is inserted through the bore 142. By inserting the stem 117 through the bore 142, the limiter 119 fits within the limiting cavity 143. The limiter 119 prevents the hook 104 from rotating completely around. The second end 132 of the first connection rod 108 is placed through the channel 140. Without tightening the bolt 144 to the threaded portion 121 of the stem 117, the clamp 110 can be moved to any position along the first connection rod 108. Similarly, the clamp 110 can be rotated about the longitudinal axis of the connection rod 108 to any angle relative to the first connection rod 108. Additionally, the first hook 104 can be rotated about the longitudinal axis of its stem 117, until the limiter 119 contacts either edge of the limiting cavity 143. It is to be understood that in another embodiment with the limiter 119 removed, the hook 109, 106 can rotate completely around until locked in position by bolt 144.

To secure both the clamp 110 to the connection rod 108 and the hook 104 to the clamp 110, the bolt 144 engages the threadable portion 121 of the stem 117. By tightening the bolt 144 the diameter of the channel 140 decreases causing and the clamp 110 to tighten around the connection rod 108. The second hook 106 is attached with the second connection rod 114 in a similar fashion.

Preferably, the hooks 104, 106 can be positioned at any angle and location along the connection rods 108, 114. Preferably, the first and second hooks 104, 106 have three degrees of freedom. The separation between the spacer 102 and the hooks 104, 106 likely differs as the distance between each is dictated by the placement of the initial opening and the location of the spinous processes. Therefore, the hooks 104, 106 will likely be positioned at different locations along the connection rods 108, 114 and at different angles relative to the spacer 102 when the spacer is urged between spinous processes and with each hook 104, 106 engage the spinous processes.

Figure 5:
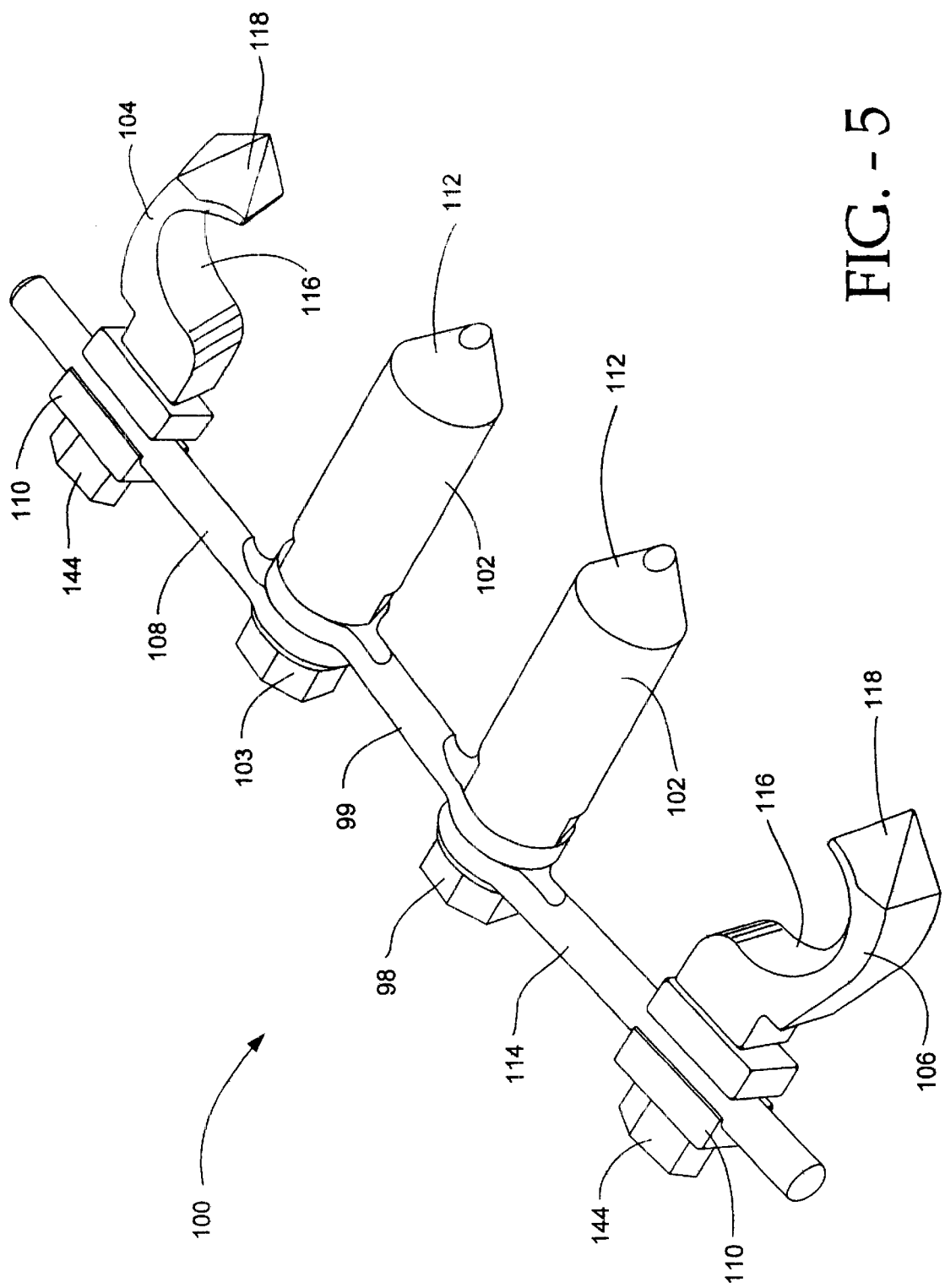
FIG. 5 is a perspective view of yet another embodiment of the present invention illustrating two spacers.

The embodiments described so far are intended to rigidly fix two spinous processes relative to one another. However, more than two vertebrae can be fused together. As illustrated by FIG. 5, the implant device 100 may contain two spacers 102. With the exception of an additional spacer 102 and a third connection rod 99 which has a bore 130 at each end, the elements of this embodiment are substantially the same as the embodiments in FIGS. 1–4. This embodiment also functions similar to the embodiment previously described above. The additional spacer 102 is connected to connecting rods 99 and 114. One of the bores 130 of the connecting rod 99 is aligned with the bore 130 of the connecting rod 114. The stem 113 of the second spacer 102 allows the bolt 98 to encircle the threaded portion 115. Tightening the bolt 98 will fasten the second spacer 102 to both the connecting rods 109, 114. Even though the remaining portion of this specification describes the present invention with only one spacer 102, the description also applies to the embodiment with multiple spacers 102.

The device 100 is designed to be implanted via a minimally invasive procedure. In a preferred method, the patient is placed in a lateral decubitus position with maximum flection of the lumbar spine. The patient can be on his or her side to insure proper orientation of the implant device 100. The implant device 100 will be preferably inserted between the spinous processes from the bottom or right side of the spinous processes to the top or left side of the spinous processes. This method permits easy visualization of the implant device 100 assembly.

Once an incision has been made and the implant area is accessible, the physician will first urge the first hook 104 between spinous processes to engage the spinous process. The physician can adjust the position of the first hook 104 so that the engagement element 116 is properly secures around the spinous process. The physician can then urge the second hook 106 between adjacent spinous processes at the same time as, or after, the first hook 104 is inserted. Similarly, the second hook 106 can be positioned so that the engagement element 116 engages the spinous process, which spinous process would be below the spacer 102. The physician can then urge the spacer 102 between adjacent spinous processes. At this point, preferably the connecting rods 108, 114 are connected to the spacer 102. The physician can attach both hooks 104, 106 to the connection rods 108, 114. This is the preferred method as the hooks should be more easily insertable about the two adjacent spinous processes prior to the spacer being inserted. This is because as the spacer is inserted between the two adjacent spinous processes, and thus generally distracts the adjacent spinous processes, the two adjacent spinous processes move closer to their respective adjacent spinous process, reducing the space where the hooks would be inserted. It is to be understood, however, that any combination of method steps of inserting and connecting together the spacer 102 and the hooks 104, 106 and the connecting rods 108, 114 fit within the spirit and scope of the invention. Thus, the hooks 104, 106 and the spacer 102 can be inserted prior to being attached to the connecting rods 108, 114. Alternatively, the connecting rods 108, 114 can be attached to the hooks 104, 106 before the hooks 104, 106 are inserted and thereafter attached to the spacer 102 after the spacer 102 is inserted.

As previously mentioned, the spacer 102 and first and second hooks 104, 106 are inserted between adjacent spinous processes from only one side. Further, securing the spinous processes by first and second hooks 104, 106 with the engagement element 116 does not require altering the spinous process. Thus, this method minimizes the damage to surrounding body tissue and promotes a faster recovery than the typical method.

The above methods use a small incision through which the pieces of the invention are inserted. However, yet another alternative method would be for the implant device 100 to be inserted through a larger incision, with the entire implant device 100 fully assembled. Prior to insertion, the bolts 103, 144 could be loosened so that the engagement portion 116 can be positioned around the spinous processes at about the same time that the spacer 102 is inserted between the spinous processes. Once this is accomplished, the spinous processes could be drawn down tightly around spacer 102, with the engagement portion 116 finally positioned around the spinous processes. All the bolts would then be tightened.

As indicated above, the implant device 100 can be implanted using a number of methods, preferably, once a primary spine fixation device is implanted between the vertebral bodies. It is to be understood, however, that this supplemented spine fixation device 100 of the invention can also be used by itself if it is desired to immobilize spinous processes relative to each other. Still alternatively as described below, another embodiment can be used with an independent spacer.

Figure 12:
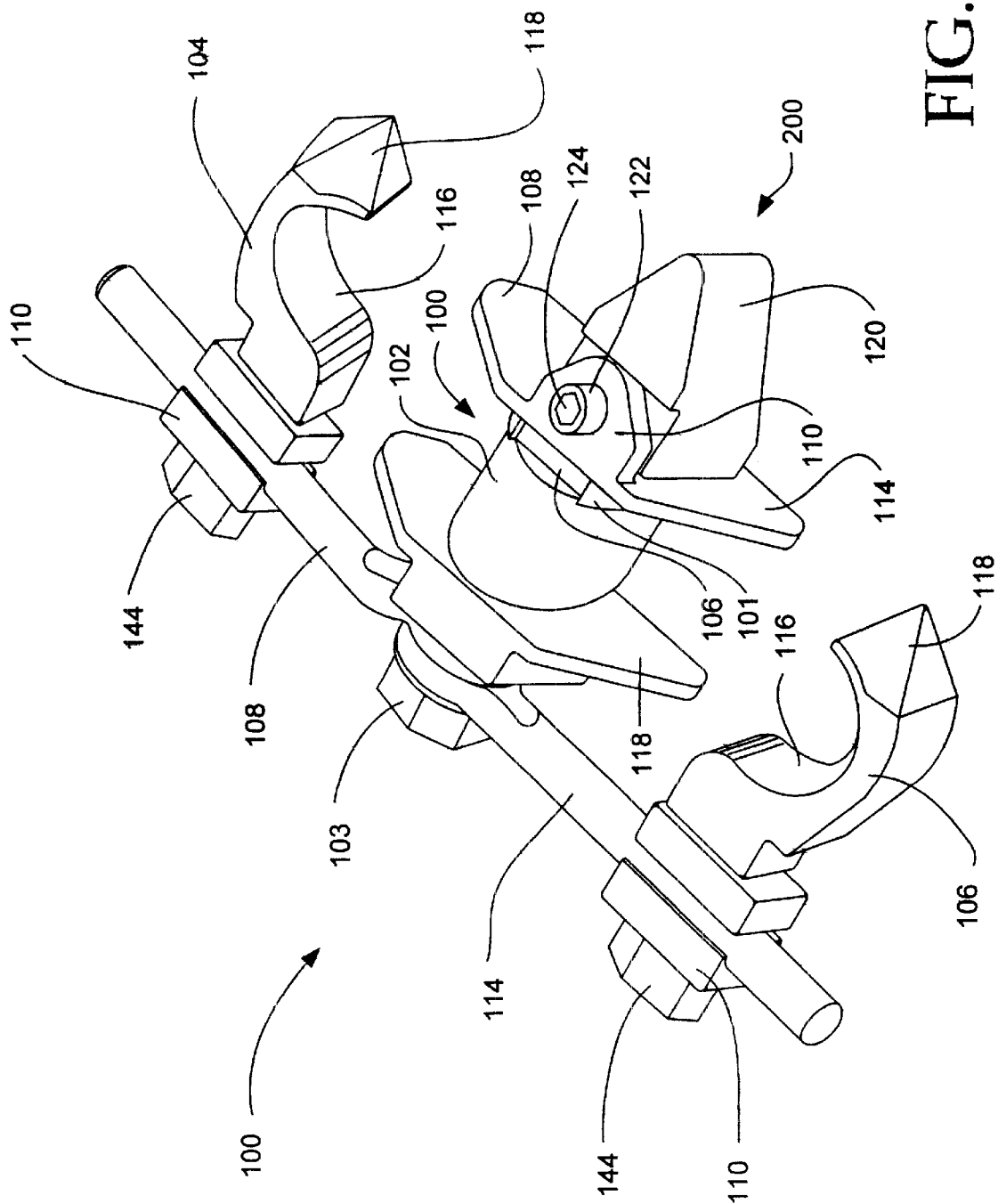
FIG. 12 depicts an alternative embodiment of the present invention used with an inventive spinous processes distractor.

As a further embodiment of the invention, the device of FIG. 1 can eliminate the body of the spacer 102 (FIG. 12) with the connecting rods 108, 114 still secured together with bolt 103 and a stem 115 with a threaded section connected to a small stop 121, that is bigger than the bore 130 in the rods. This arrangement would keep the connecting rods 108, 114 together and allow them to rotate relative to each other until the bolt 103 is tightened. This device is used to limit the spreading apart of the spinous processes during flexion or forward bending. As can be seen in FIG. 12, this embodiment of the invention can be used, if desired with an inventive interspinous process distraction system 200 such as any of the variety of systems presented by the present assignee. These systems 200 are more fully described in the patents and patent applications referenced and incorporated herein under the cross-reference section.

Figure 8A:
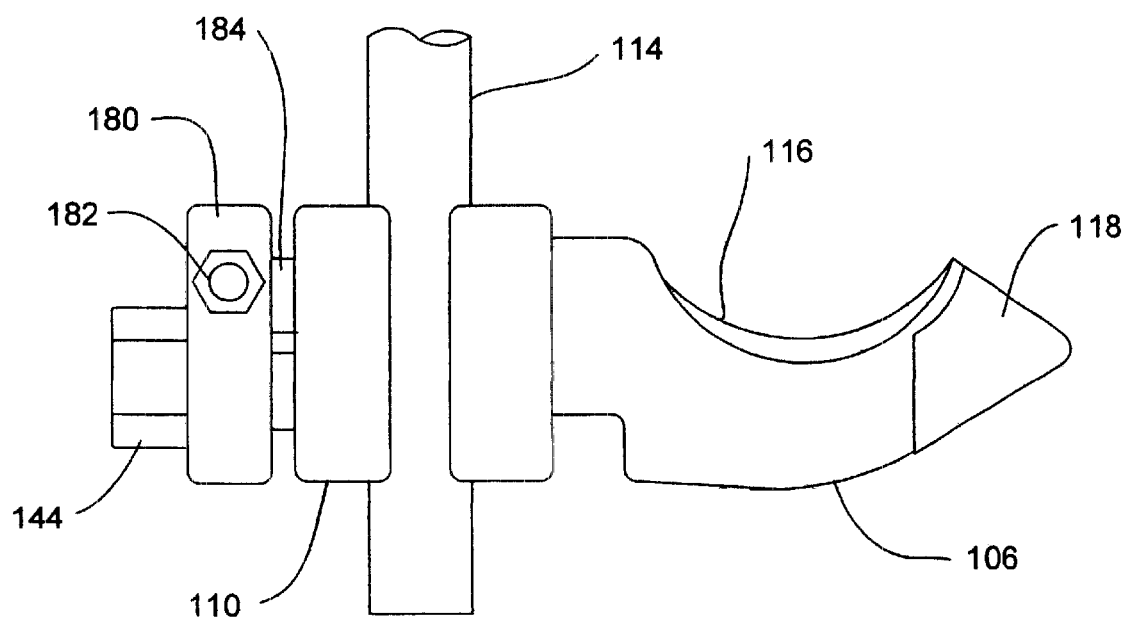
FIG. 8a is a side view showing a portion of this alternative embodiment.

FIGS. 8 and 8a depict an alternative embodiment of the invention wherein the fastening and tightening bolts 103 and 144 are supplemented with alternative bolts such as bolt 182 in FIG. 8a. These bolts are mounted at approximate 90 degrees to the other bolts 103, 144 in order to allow the surgeon to tightened these bolts while looking at them head on, as opposed to looking at them from the side as would be the case with bolts 103, 144. This is thus more convenient for the physician to assemble and tightened. As shown in FIG. 8a, for this arrangement, the clamp 110 includes an additional clamp element 180. In this additional clamp element 180 another bolt as indicated above, bolt 182 is mounted. This bolt is essentially either a quarter or half turn bolt such that when the bolt is turned either a quarter or a half turn, a caming member 184 extends from the clamp member 180 in order to be urged against the adjacent clamp member, tightening that clamp member against the connecting rod 114. In operation, the hook 106 and clamp 110 would be preassembled and then at the surgical site slid over the connecting rod 114. After the hook 106 is positioned between spinous processes, the nut 182 can be turned in order to extend the caming member 184 from the clamp element 180 against the remainder of the clamp 110 in order to lock the hook 106 in place on the connecting rod 114. It is to be understood that a similar arrangement can be accomplished with respect to the clamp mechanism which holds the spacer 102 to the connecting rods 108, 114.

As yet a further embodiment of the invention, the device of FIG. 1 can be modified to eliminate the second connecting rod 114 and the second hook 106 with the engagement element 116. In this embodiment, the engagement portion 116 of the first hook 104 serves to keep the spacer 102 in place between adjacent spinous processes. So configured, the inventive device 100 aids to limit extension without inhibiting flexion or focused bending.

The foregoing description of preferred embodiments of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. An implant device for rigidly fixing adjacent spinous process, the device comprising:
   at least one spacer, wherein the spacer is adapted for urging between spinous process;
   a first and a second engagement element, each element adapted to engage a spinous process;
   a first and second connection rods;
   whereby the first and second connection rods are movably connected with the spacer; and
   whereby the first and second engagement members are fastened to the first and second connection rods respectively.

2. The device according to claim 1, whereby the spacer is substantially circular in shape.

3. The device according to claim 1, whereby the spacer is substantially egg-shaped.

4. The device according to claim 1, whereby the first and second engagement elements have a tapered front end adapted for urging the first and second engagement elements between adjacent spinous process.

5. The device according to claim 1, whereby the first and second connection rods pivot about a longitudinal axis of the spacer.

6. The device according to claim 5, whereby the first and second connection rods pivot independently of each other.

7. The device according to claim 1, whereby the engagement elements are fastened to the connection rods so that the engagement elements can be positioned at selected locations along the length of the connection rods.

8. The device according to claim 1, whereby the engagement members can be positioned at an angle relative to the connection rods.

9. The device according to claim 4, whereby the first and second engagement members further each have a hook element that is adapted for engaging the spinous process once the tapered front end has been urged between spinous process.

10. The device according to claim 1, wherein the spacer has a tapered front end.

11. The device of claim 1, wherein at least one of the engagement elements is rotatable.

12. The device of claim 1, wherein the spacer is elliptical in shape.

13. The device of claim 1, wherein the spacer has anatomically compatible contours.

14. An implant device for rigidly fixing adjacent spinous process, the device comprising:
   at least one spacer, wherein the spacer further contains a tapered front end adapted for urging the spacer between adjacent spinous process;
   a plurality of engagement elements, each adapted to engage a spinous process;

a plurality of connection rods;

whereby the connection rods are selectively movably connected with the spacer; and whereby the engagement members are fastened to the connection rods, and further are positionably located along the length of the connection rods.

15. The device according to claim 14, whereby the spacer is substantially circular in shape.

16. The device according to claim 14, whereby the spacer is substantially egg-shaped.

17. The device according to claim 14, whereby the engagement elements further have a tapered front end adapted for urging the engagement elements between adjacent spinous process.

18. The device according to claim 14, whereby the connection rods pivot about the longitudinal axis of the spacer.

19. The device according to claim 18, whereby the connection rods pivot independently of each other.

20. The device according to claim 14, whereby the engagement members can further be positioned at any angle relative to the connection rods.

21. The device according to claim 17, whereby the engagement members further have a hook element that is adapted for engaging the spinous process once the tapered front end has been urged between spinous process.

22. The device according to claim 14, wherein at least one of said engagement elements is rotatable.

23. The device of claim 14, wherein the spacer is elliptical in shape.

24. The device of claim 14, wherein the spacer has anatomically compatible contours.

25. An implant device for rigidly fixing adjacent spinous process, the device comprising:

at least one spacer, wherein the spacer further contains a tapered front end adapted for urging the spacer between adjacent spinous process;

a plurality of rotatable engagement elements each adapted to engage a spinous process;

a plurality of connection rods;

whereby the connection rods are movably connected with the spacer; and whereby the engagement members are selectively locatable at positions along the length of the connection rods.

26. The device according to claim 25, whereby the spacer is substantially circular in shape.

27. The device according to claim 25, whereby the spacer is substantially elliptical in shape.

28. The device according to claim 25, whereby the rotatable engagement elements further have a tapered front end adapted for urging the engagement elements between adjacent spinous process.

29. The device according to claim 25, whereby the connection rods pivot about a longitudinal axis of the spacer.

30. The device according to claim 29, whereby the connection rods pivot independently of each other.

31. The device according to claim 25, whereby the engagement members can further be positioned at any angle relative to the connection rods.

32. The device according to claim 28, whereby the engagement members further have a hook element that is adapted for engaging the spinous process once the tapered front end has been urged between spinous process.

33. The device according to claim 25, wherein said spacer is rotatable.

34. The device of claim 25, wherein the spacer is elliptical in shape.

35. The device of claim 25, wherein the spacer has anatomically compatible contours.

36. An implant device for rigidly fixing adjacent spinous process, the device comprising:

at least one spacer, wherein the spacer is adapted for being urged between adjacent spinous process;

a plurality of rotatable engagement elements, each adapted to each engage a spinous process;

a plurality of connection rods;

whereby the spacer is connected with the connection rods; and whereby the engagement members are fastened to the connection rods, and further can be positioned at any location along the length of the connection rods.

37. The device according to claim 36, whereby the spacer is substantially circular in shape.

38. The device according to claim 36, whereby the spacer is substantially elliptical in shape.

39. The device according to claim 36, whereby the rotatable engagement elements further have a tapered front end adapted for urging the engagement elements between adjacent spinous process.

40. The device according to claim 36, whereby the connection rods pivot independently of each other.

41. The device according to claim 36, whereby the rotatable engagement members can further be positioned at any angle relative to the connection rods.

42. The device according to claim 40, whereby the engagement members further have a hook element that is adapted for engaging the spinous process once the tapered front end has been urged between adjacent spinous process.

43. The device of claim 36, wherein the spacer is elliptical in shape.

44. The device of claim 36, wherein the spacer has anatomically compatible contours.

45. An implant device for rigidly fixing adjacent spinous process, the device comprising:

a plurality of rotatable engagement elements adapted to each engage a spinous process;

a plurality of connection rods which are movable with respect to each other;

whereby the engagement members are fastened to the connection rods, and are locatable at positions along the length of the connection rods.

46. The device of claim 45 including a means for movably mounting the connecting rods to each other.

47. The device according to claim 45, whereby the rotatable engagement elements further have a tapered front end adapted for urging the engagement elements between adjacent spinous process.

48. The device according to claim 45, whereby the connection rods pivot independently of each other.

49. The device according to claim 45, whereby the rotatable engagement members can further be positioned at any angle relative to the connection rods.

50. The device according to claim 45, whereby the engagement members further have a hook element that is adapted for engaging the spinous process once the tapered front end has been urged between spinous process.

51. A method to rigidly fix adjacent spinous process, the method comprising the steps of:

(a) urging a first engagement element between adjacent spinous process;

(b) adjusting the position of the first engagement element such that the first engagement element engages the spinous process;

(c) urging a second engagement element between adjacent spinous process;
(d) adjusting the position of the second engagement element such that the second engagement element engages the spinous process;
(e) urging a spacer between adjacent spinous process; and
(f) fastening the first and second engagement elements to connection rods that are pivotally mounted to the spacer, thus securing the spacer relative to the first and second engagement elements.

52. The method according to claim 51, whereby the spacer in step (e) contains a tapered front end adapted so that the spacer may be urged between adjacent spinous process.

53. The method according to claim 51, whereby the first engagement element in step (a) contains a tapered front end adapted so that the first engagement element may be urged between adjacent spinous process.

54. The method according to claim 51, whereby the second engagement element in step (c) contains a tapered front end adapted so that the second engagement element may be urged between adjacent spinous process.

55. The method according to claim 51, whereby fastening the first and second engagement elements to a connection rod in step (f) is accomplished by a clamp device adapted to fasten to the connection rod, and further to allow the first and second engagement element to rotate.

56. The method according to claim 51, whereby urging the spacer between adjacent spinous process in step (e) is accomplished by inserting the spacer from only one side, thus minimizing the damage to surrounding body tissue.

57. The method according to claim 51, whereby securing the first and second engagement elements to the spinous process in steps (b) and (d) does not require altering the spinous process.

58. An implant device for rigidly fixing adjacent spinous process, the device comprising:
at least one spacer;
a plurality of rotatable engagement elements, each adapted to engage a spinous process;
a plurality of connection rods;
means for moving the connection rods relative to the spacer; and
means for connecting the rotatable engagement elements with the connection rods.

59. The device according to claim 58, whereby the spacer is substantially elliptical in shape.

60. The device according to claim 58, whereby the spacer is substantially egg shaped.

61. The device according to claim 58, whereby the connecting means include rotatable engagement elements being movably connected to said connection rods.

62. The device according to claim 58, wherein the connection rods are rotatably connected to the spacer.

63. The device of claim 58, wherein said spacer includes means for allowing the spacer to be urged between adjacent spinous processes.

64. The device of claim 58, wherein at least one of said rotatable engagement elements has means for allowing the element to be urged between adjacent spinous processes.

65. The device of claim 58, wherein the spacer is elliptical in shape.

66. The device of claim 58, wherein the spacer has anatomically compatible contours.

67. An implant device for rigidly fixing adjacent spinous processes, the device comprising:
a first and a second spacer, each adapted for urging between adjacent spinous processes;
a first and a second engagement element, each adapted for urging between adjacent spinous processes;
a first and a second connection rod movably mounted to the first spacer;
a third connection rod along with the second connection rod movably mounted to the second spacer; and
whereby the first and the second engagement elements are fastened to the first and the third connection rod respectively.

68. The device according to claim 67, wherein the first and second spacer is substantially circular in shape.

69. The device according to claim 67, wherein the first and second spacer is substantially egg-shaped.

70. The device according to claim 67, whereby the first and second rotatable engagement elements have a tapered front end adapted for urging the first and second engagement elements between adjacent spinous process.

71. The device according to claim 67, whereby the first and second connection rods pivot independently of each other.

72. The device according to claim 67, whereby the engagement elements are fastened to the connection rods so that the engagement elements can be positioned at any location along the length of the connection rods.

73. The device according to claim 67, whereby the engagement members can further be positioned at an angle relative to the connection rods.

74. The device according to claim 70, whereby the first and second engagement members further each have a hook element that is adapted for engaging the spinous process once the tapered front end has been urged between spinous process.

75. The device according to claim 67, wherein the spacer has a tapered front end.

76. The device according to claim 67, wherein the engagement elements are rotatable.

77. The device of claim 67, wherein the spacers are elliptical in shape.

78. The device of claim 67, wherein the spacers have anatomically compatible contours.

79. An implant device for rigidly fixing adjacent spinous process, the device comprising:
at least one spacer, wherein the spacer is adapted for urging between spinous process;
a first engagement element, said element adapted to engage a spinous process;
a first rod;
whereby the first connection rod is movably connected with the spacer; and
whereby the first engagement member is fastened to the first connection rod respectively.

80. An implant device for rigidly fixing adjacent spinous process, the device comprising:
at least one spacer, wherein the spacer further contains a tapered front end adapted for urging the spacer between adjacent spinous process;
an engagement element adapted to engage a spinous process;
a connection rod;
whereby the connection rod is selectively movably connected with the spacer; and
whereby the engagement member is fastened to the connection rod, and further are positionably located along the length of the connection rod.

81. An implant device for rigidly fixing adjacent spinous process, the device comprising:

at least one spacer, wherein the spacer further contains a tapered front end adapted for urging the spacer between adjacent spinous process;

an engagement element adapted to engage a spinous process;

a connection rod;

whereby the connection rod is movably connected with the spacer; and whereby the engagement member is selectively locatable at positions along the length of the connection rod.

82. An implant device for rigidly fixing adjacent spinous process, the device comprising:

at least one spacer, wherein the spacer is adapted for being urged between adjacent spinous process;

an engagement element adapted to engage a spinous process;

a connection rod;

whereby the spacer is connected with the connection rod; and whereby the engagement member is fastened to the connection rod, and further can be positioned at any location along the length of the connection rod.

83. An implant device for rigidly fixing adjacent spinous process, the device comprising:

at least one spacer, an engagement element adapted to engage a spinous process;

a connection rod;

means for rotating the connection rod relative to the spacer; and means for connecting the engagement element with the connection rod.

84. The device of claim 45 including:

an separate spacer adapted for insertion between adjacent spinous processes.

85. The device of claim 45 including:

a spacer that is not connected to the connection rods and which includes a cylindrical body with a stop, which spacer is adapted for insertion of the body between adjacent spinous processes with the stop limiting the motion of the spacer relative to the spinous processes.

86. The device of claim 1 wherein said engagement elements have a length and a fastener that can fasten said engagement elements to the connection rods, which fastener is located along the length of the engagement elements.

87. The device of claim 1 wherein said engagement elements have a length and a fastener that can fasten said engagement elements to the connection rods, which fastener is located at an angle to the length of the engagement elements.

88. The device of claim 1 wherein said engagement elements have a length and a fastener that can fasten said engagement elements to the connection rods, which fastener is rotated about the axis of the length of the engagement element in order to tighten the engagement elements to the connection rods.

89. The device of claim 1 wherein said engagement elements have a length and a fastener that can fasten said engagement elements to the connection rods, which fastener is rotated at an angle to the axis of the length of the engagement element in order to tighten the engagement elements to the connection rods.

90. The device of claim 1 wherein at least one of the engagement elements is rotatably relative to the connection rods and including a mechanism that limits the rotation of the at least one of the engagement elements.

91. The device of claim 14 wherein said engagement elements have a length and a fastener that can fasten said engagement elements to the connection rods, which fastener is located along the length of the engagement elements.

92. The device of claim 14 wherein said engagement elements have a length and a fastener that can fasten said engagement elements to the connection rods, which fastener is located at an angle to the length of the engagement elements.

93. The device of claim 14 wherein said engagement elements have a length and a fastener that can fasten said engagement elements to the connection rods, which fastener is rotated about the axis of the length of the engagement element in order to tighten the engagement elements to the connection rods.

94. The device of claim 14 wherein said engagement elements have a length and a fastener that can fasten said engagement elements to the connection rods, which fastener is rotated at an angle to the axis of the length of the engagement element in order to tighten the engagement elements to the connection rods.

95. The device of claim 14 wherein at least one of the engagement elements is rotatably relative to the connection rods and including a mechanism that limits the rotation of the at least one of the engagement elements.

96. The device of claim 25 wherein said engagement elements have a length and a fastener that can fasten said engagement elements to the connection rods, which fastener is located along the length of the engagement elements.

97. The device of claim 25 wherein said engagement elements have a length and a fastener that can fasten said engagement elements to the connection rods, which fastener is located at an angle to the length of the engagement elements.

98. The device of claim 25 wherein said engagement elements have a length and a fastener that can fasten said engagement elements to the connection rods, which fastener is rotated about the axis of the length of the engagement element in order to tighten the engagement elements to the connection rods.

99. The device of claim 25 wherein said engagement elements have a length and a fastener that can fasten said engagement elements to the connection rods, which fastener is rotated at an angle to the axis of the length of the engagement element in order to tighten the engagement elements to the connection rods.

100. The device of claim 25 wherein at least one of the engagement elements is rotatably relative to the connection rods and including a mechanism that limits the rotation of the at least one of the engagement elements.

101. A method to rigidly fix spinous processes including the steps of:

urging a first engagement element into engagement with a first spinous process;

urging a second engagement element into engagement with a second spinous process;

urging a spacer between the first and the second spinous process; and using connecting rods to connect the spacer with the first and the second engagement elements.

102. A method to rigidly fix spinous processes including the steps of:

urging a first engagement element into engagement with a first spinous process;

urging a second engagement element into engagement with a second spinous process;

urging an independent spacer between the first and the second spinous process; and using connecting rods to connect the first and the second engagement elements.

103. The method of claim 101 wherein the steps are conducted in any order.

104. The method of claim 102 wherein the steps are conducted in any order.

105. The method of claim 51 wherein the steps are conducted in any order.

* * * * *